United States Patent [19]

Mukai et al.

[11] Patent Number: 4,983,644
[45] Date of Patent: Jan. 8, 1991

[54] DENTAL ADHESIVE COMPOSITION

[75] Inventors: Nobuhiro Mukai, Hiroshima; Hitoshi Ige, Ohtake; Takayuki Makino, Ohtake; Junko Atarashi, Ohtake, all of Japan

[73] Assignee: Mitsubishi Rayon Company, Limited, Tokyo, Japan

[21] Appl. No.: 340,804

[22] Filed: Apr. 20, 1989

[30] Foreign Application Priority Data

Jun. 21, 1988 [JP] Japan ................................ 63-152974

[51] Int. Cl.$^5$ ................................ C08F 2/46
[52] U.S. Cl. ........................ 522/14; 522/68; 522/96; 522/103; 522/171; 522/172; 523/120
[58] Field of Search ................ 523/120; 528/28; 522/103, 96, 172, 14, 68, 171

[56] References Cited

U.S. PATENT DOCUMENTS

| | | | |
|---|---|---|---|
| 2,367,660 | 1/1945 | Agre. | |
| 3,847,767 | 11/1974 | Kloczewski. | |
| 4,097,994 | 7/1978 | Reaville et al. | 522/103 |
| 4,138,299 | 2/1979 | Bolgiano | 522/96 |
| 4,159,369 | 6/1979 | Blount | 528/28 |
| 4,374,237 | 2/1983 | Berger et al. | 528/28 |
| 4,388,069 | 6/1983 | Orlowski | 522/103 |
| 4,540,723 | 9/1985 | Ying | 522/103 |
| 4,579,881 | 4/1986 | Masuhara et al. | 523/120 |
| 4,593,054 | 6/1986 | Asmussen et al. | 523/120 |
| 4,657,959 | 4/1987 | Bryan et al. | 523/120 |
| 4,798,878 | 1/1989 | Brinkmann et al. | 528/28 |
| 4,908,297 | 3/1990 | Head et al. | 522/96 |

FOREIGN PATENT DOCUMENTS

| | | |
|---|---|---|
| 0017151 | 10/1980 | European Pat. Off. . |
| 0059649 | 9/1982 | European Pat. Off. . |
| 0104000 | 3/1984 | European Pat. Off. . |
| 2506650 | 8/1976 | Fed. Rep. of Germany . |
| 408265 | 3/1934 | United Kingdom . |
| 569974 | 2/1945 | United Kingdom . |

OTHER PUBLICATIONS

Chemical Abstracts, vol. 52, No. 4, Feb. 25, 1958, column 2566b, Columbus, Ohio (US).
Polymer Science and Technology, vol. 14, 1981, Plenum, New York (US), p. 411–417.

*Primary Examiner*—Morton Foelak
*Assistant Examiner*—Dennis R. Daley
*Attorney, Agent, or Firm*—Oblon, Spivak, McClelland, Maier & Neustadt

[57] ABSTRACT

A dental adhesive composition containing as major components:
(a) at least one isocyanate-group-containing urethane prepolymer,
(b) at least one isocyanate-group-containing silane compound,
(c) at least one radical-polymerizable unsaturated monomer, and
(d) at least one initiator selected from the group consisting of redox polymerization initiators and photopolymerization initiators is disclosed.

This composition is excellent in bonding properties when it is used to bond a living dental tissue with a restoring material such as a metal, organic polymer, and ceramic. Also, this adhesive composition does not require a troublesome pretreatment of the restoring material with an etching agent such as phosphoric acid when the restorating material is required to bond to the living tissue.

10 Claims, No Drawings

DENTAL ADHESIVE COMPOSITION

BACKGROUND OF THE INVENTION

1. Field of the Invention

The present invention relates to a dental adhesive composition that is excellent in bonding properties and will be used to bond such restorative materials for a living dental tissues as metals, organic polymers, and ceramics to the dental tissues.

2. Description of the Prior Art

In the field of dental materials, a variety of materials have been used for restorating carious teeth and missing teeth. Such materials include metals such as gold, silver, platinum, alloy, and amalgam; organic high polymers such as polymethyl methacrylates, polycarbonates, cured products of polyfunctional vinyl monomers, and composite resins comprising such polymers and fillers; ceramics such as porcelain. However, these materials hardly adhere to the living dental tissues. Therefore, dental adhesive compositions containing, as an adhesive component, a compound having polar groups such as a phosphate group, a hydroxyl group, and an acid anhydride group have been proposed to improve adhesion or bonding between inorganic components such as calcium phosphate (e.g., hydroxy apatite) or organic components such as collagen that form the tooth tissues with the restorative materials.

However, the adhesive containing the phosphate group, hydroxyl group, or acid anhydride group as a functional group had a disadvantage that bonding property to the dentine was not observed at all. This is attributed to the fact that dentine is not an object suitable for bonding with the adhesive containing the functional groups because the protein content in the dentine is considerably high in comparison with the enamel and because a number of dentinal tubules filled with body fluid exist in the dentine. Therefore, when the above prior adhesives are used, a pretreatment of the apatite of the tissue with an etching agent such as phosphoric acid was necessary. Such pretreatment, however, is not only troublesome but also has a problem that the treatment hurts teeth. Besides, bond strength between the tissues and restorative materials is insufficient even when the pretreatment was conducted, and long spells of the pretreatment may not be adopted, due to the problem of harming the teeth. Therefore, there was a disadvantage in that a gap occurs between the restorative material and the dentine after a long period of time even if teeth were restored with the prior adhesives containing the polar groups, and in some cases, the restorative material comes off.

SUMMARY OF THE INVENTION

The object of the present invention is to provide a dental adhesive composition which has a practically sufficient bond strength without requiring the troublesome pretreatment with an etching agent such as phosphoric acid which pretreatment was essential in bonding the living dental tissue, in particular, dentine and the restorative material together in the prior art.

Therefore, a dental adhesive composition of the present invention comprises:

(a) at least one isocyanate-group-containing urethane prepolymer, (b) at least one isocyanate-group-containing silane compound, (c) at least one radical-polymerizable unsaturated monomer, and (d) at least one initiator selected from the group consisting of redox polymerization initiators and photopolymerization initiators.

DESCRIPTION OF THE PREFERRED EMBODIMENTS

The isocyanate-group-containing urethane prepolymer that is the component (a) used in the present invention is a prepolymer obtained by reacting a polyol with a polyfunctional isocyanate compound having two or more isocyanate groups under such conditions that a part of the isocyanate groups remain in the resulting compound. As the polyol, either polyether polyol and polyester polyol can be used, and the polyol preferably has a hydroxyl group at the ends.

The polyether polyol can be obtained by reacting alkylene oxide such as ethylene oxide, propylene oxide, and butylene oxide with at least one compound selected from ethylene glycol, propylene glycol, and 1,6-hexane diol by addition polymerization.

The polyester polyol can be prepared by condensation of a dibasic acid such as adipic acid with a glycol such as ethylene glycol under a condition that the glycol is used in excess amount.

Of these polyols, polyether polyols comprising only propylene glycol units or comprising both polypropylene glycol unit and ethylene glycol unit are preferable. The polyols may be block copolymers or random copolymers. In the case of polyols having both units, the ratio of ethylene glycol unit in total of the propylene glycol unit and ethylene glycol unit is preferably 40 to 80 mol % since a resulting urethane prepolymer becomes hydrophilic or water-soluble.

As the polyfunctional isocyanate compound, a compound having two or more isocyanate groups in the molecule can be used. As the isocyanate, tolylene diisocyanate, 4,4-diphenylmethane diisocyanate, and hexamethylene diisocyanate are preferable, since isocyanate-group-containing urethane prepolymer having a high bond strength can be obtained when such diisocyanates were used.

The molecular weight of the urethane prepolymer containing isocyanate groups used in the present invention is preferably 400 to 50,000, more preferably 400 to 20,000 with a view to obtain good solubility in the radical-polymerizable unsaturated monomer and excellent bonding properties.

These urethane prepolymers preferably have an isocyanate group at each end in view of the fact that bonding properties of the dentine with the restorative material is exhibited by the reaction of the isocyanate groups present in the urethane prepolymer with organic components (particularly collagen containing a number of active hydrogen groups in the molecule) in the living dental tissue, in particular the dentine, and with water (the body fluid).

While the isocyanate-group-containing urethane prepolymer can be used alone, it also may be used together with a diluent that is inert to the isocyanate groups in order to make workability of the composition facile at the time when it is used. Such diluent includes acetone, methyl ethyl ketone, ethyl acetate, toluene, xylene, and trichloroethane.

An isocyanate-group-containing silane compound that is a component (b) in the present invention is used to improve the storage stability and the bonding properties of the adhesive composition. Depending on the amount of the silane compound to be used, it is possible to reduce the amount of the diluent for the urethane prepolymer containing isocyanate groups.

Examples of the isocyanate-group-containing silane compound in the present invention include silane compounds having at least one isocyanate group. Among the compounds, silane compounds having the following structural formula (1) or (2):

$$OCN-(CH_2)_n-\underset{\underset{(CH_3)_{3-m}}{|}}{Si}-(OR)_m \quad (1)$$

(wherein n is an integer of 1 to 10, m is 2 or 3, and R represents methyl group, ethyl group, $-OC_2H_4OCH_3$, or $-Cl$)

$$R'_p-Si(NCO)_{4-p} \quad (2)$$

(wherein p in an integer of 0 to 3, R' represents methyl group, ethyl group, ethoxy group, phenyl group, vinyl group, α-methyl vinyl group, methacryloyloxyethyl group, acryloyloxyethyl group, methacryloyloxypropyl group, or acryloyloxypropyl group) are preferable. Examples of the silane compounds of the formula (1) include:

OCH—(CH$_2$)$_2$—Si—(OCH$_3$)$_3$, OCN—(CH$_2$)$_2$—Si—(OCH$_3$)$_2$,
                                            |
                                           CH$_3$

OCN—(CH$_2$)$_3$—Si—(OCH$_3$)$_3$, OCN—(CH$_2$)$_3$—Si—(OCH$_3$)$_2$,
                                            |
                                           CH$_3$

OCN—(CH$_2$)$_5$—Si—(OCH$_3$)$_3$, OCN—(CH$_2$)$_5$—Si—(OCH$_3$)$_2$,
                                            |
                                           CH$_3$

OCN—(CH$_2$)$_9$—(OCH$_3$)$_3$, OCN—(CH$_2$)$_9$—Si—(OCH$_3$)$_2$
                                            |
                                           CH$_3$

OCN—(CH$_2$)$_2$—Si—(OC$_2$H$_5$)$_3$, OCN—(CH$_2$)$_2$—Si—(OC$_2$H$_5$)$_2$
                                            |
                                           CH$_3$

OCN—(CH$_2$)$_3$—Si—(OC$_2$H$_5$)$_3$, OCN—(CH$_2$)$_3$—Si(—OC$_2$H$_5$)$_2$,
                                            |
                                           CH$_3$

OCN—(CH$_2$)$_2$—Si—(OC$_2$H$_4$OCH$_3$)$_3$, OCN—(CH$_2$)$_2$—Si—Cl$_3$

OCN—(CH$_2$)$_2$—Si—(OC$_2$H$_4$OCH$_3$)$_2$, OCN—(CH$_2$)$_2$—Si—Cl$_2$
              |                                        |
             CH$_3$                                     CH$_3$

OCH—(CH$_2$)$_3$—Si—(OC$_2$H$_4$OCH$_3$)$_3$, OCN—(CH$_2$)$_3$—Si—Cl$_3$,

OCN—(CH$_2$)$_3$—Si—(OC$_2$H$_4$OCH$_3$)$_2$, and
              |
             CH$_3$ -continued OCN—(CH$_2$)$_3$—Si—Cl$_2$,
              |
             CH$_3$ Example of the silane compounds of the formula (2) include:
Si(NCO)$_4$, CH$_3$Si(NCO)$_3$, (CH$_3$)$_2$Si(NCO)$_2$, (CH$_3$)$_3$Si(NCO), C$_2$H$_5$Si(NCO)$_3$, (C$_2$H$_5$)$_2$Si(NCO)$_2$, (C$_2$H$_5$)$_3$Si(NCO), C$_2$H$_5$OSi(NCO)3, C$_6$H$_5$Si(NCO)$_3$, (C$_2$H$_{5l\ O})_2$ (C$_2$H$_5$O)$_2$Si(NCO)$_2$, (C$_2$H$_5$O)$_3$Si(NCO), CH$_2$=CHSi(NCO)$_3$, CH$_2$=CCH$_3$Si(NCO)$_3$, CH$_2$=CHCOOC$_3$H$_6$Si(NCO)$_3$, CH$_2$=CCH$_3$COOC$_3$H$_6$Si(NCO)$_3$.

Of these compounds,

OCN—(CH$_2$)$_3$—Si—(OCH$_3$)$_3$, OCN—(CH$_2$)$_3$—Si—(OCH$_3$)$_2$,
                                            |
                                           CH$_3$

OCN—(CH$_2$)$_3$—Si(—OC$_2$H$_5$)$_3$, OCN—(CH$_2$)$_3$—Si—(OC$_2$H$_5$)$_2$,
                                            |
                                           CH$_3$

CH$_2$=CHSi(NCO)$_3$ (vinylsilyl triisocyanate), CH$_2$=CCH$_3$COOC$_3$H$_6$Si(NCO)$_3$ (γ-methacryloyloxypropylsilyl triisocyanate), (CH$_3$)$_3$Si(NCO) (trimethylsilyl isocyanate), (CH$_3$)$_2$Si (NCO)$_2$ (dimethylsilyl diisocyante), and (CH$_3$)Si(NCO)$_3$ (methylsilyl triisocyanate) are preferable.

The radical-polymerizable unsaturated monomer that is the component (c) used in the present invention is a component which is necessary to quickly harden the adhesive composition by redox polymerization, or by irradiation of light in the presence of a photopolymerization initiator in case of using a photopolymerization initiator as the polymerization initiator. Use of the radical-polymerizable unsaturated monomer is important when the composition is required to quickly harden as it is worked in the mouth.

As the radical-polymerizable unsaturated monomer, any monomer that does not prevent the reaction of the isocyanate-group-containing urethane prepolymer with the dentine can be used.

As the monomer, both monofunctional monomer and polyfunctional monomer can be used.

Examples of the monofunctional unsaturated monomers include methyl (meth)acrylate, ethyl (meth)acrylate, propyl (meth)acrylate, butyl (meth)acrylate, pentyl (meth)acrylate, hexyl (meth)acrylate, 2-hydroxyethyl (meth)acrylate, vinyl acetate, styrene, acrylonitrile, glycidyl methacrylate, and benzyl methacrylate.

Example of the polyfunctional unsaturated monomer include ethylene glycol di(meth)acrylate, polyethylene glycol di(meth)acrylate having 2 to 20 ethylene glycol units, 1,6-hexanediol di(meth)-acrylate, neopentyl glycol di(meth)acrylate, trimethylolpropane tri(meth)acrylate, bisphenol A bis(meth)acrylates represented by the following general formulas:

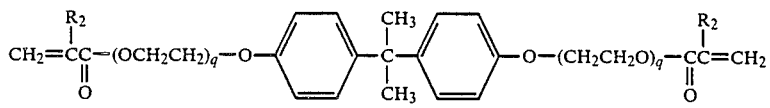

(wherein R$_2$ represents a hydrogen atom or a methyl group, and q is an integer of 1 to 20)

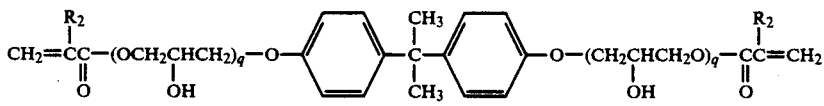

(wherein $R_2$ and q are the same as those in the formula explained just above), hexafunctional urethane methacrylates represented by the following general formula:

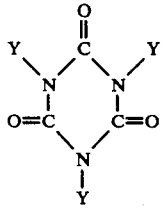

(wherein Y is

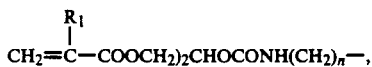

$R_1$ represents hydrogen atom or methyl group, and may be the same or different, and n is an integer of 1 to 10), and

(wherein $R_3$ represents hydrogen atom or methyl group, and may be the same or different, and X represents alkylene group having 1 to 6 carbon atoms or

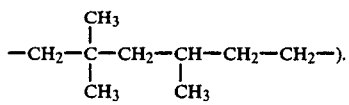

Of the monofunctional unsaturated monomers mentioned above, methyl (methyl)acrylate, 2-hydroxy-ethyl methacrylate, and benzyl methacrylate are preferably used.

Of the polyfunctional unsaturated monomers, ethylene glycol di(meth)acrylate, triethylene glycol di(meth)acrylate, nonaethylene glycol di(meth)acrylate, tetradecaethylene glycol di(meth)acrylate, trimethylolpropane trimethacrylate, 1,6-hexanediol di(meth)acrylate, bisphenol A bismethacrylates represented by the formulas shown above wherein $R_2$ is a methyl group, 1,2-bis[3-(meth)-acryloyloxy-2-hydroxy-propoxy]ethane, and 1,4-bis[3-(meth)-acryloyloxy-2-hydroxypropoxy]butane, hexafunctional urethane methacrylates represented by the formula shown above and wherein all $R_1$ are methyl groups (hereinafter abbreviated to U-6H),

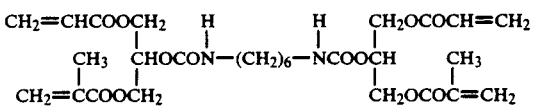

(hereinafter abbreviated to U-4HA) and

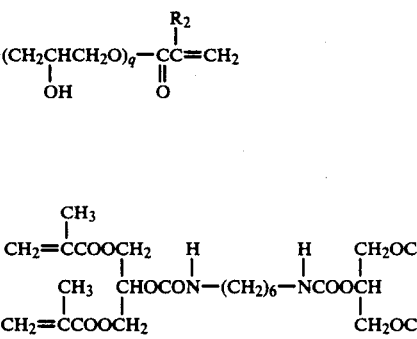

(hereinafter abbreviated to U-4H) can preferably be used.

In the present invention, a polymerizable phosphate that is an ester of phosphoric acid having a polymerizable unsaturated bond as an alcoholic component in the ester can be used as a polymerizable unsaturated monomer in place of, or in combination with the monofunctional and/or polyfunctional monomers.

Examples of the polymerizable phosphates include

(wherein $R_2$ represents hydrogen atom or methyl group, and r is 2, 3, 5, 9, or 12) and

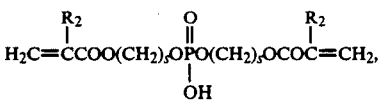

(wherein $R_2$ represents hydrogen atom or methyl group, and s is 2, 3, or 5).

Of these,

(methacryloyloxyethyl phosphate) and

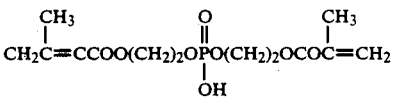

(dimethacryloyloxyethyl phosphate) are most preferably used.

The amount of the polymerizable phosphoric acid ester to be used is generally 0.1 to 30% by weight, preferably 0.5 to 10% by weight, and more preferably 1.0 to 5.0% by weight of the total amount of the radical-polymerizable unsaturated monomers.

Although as the photopolymerization initiator that is component (d) of the present invention, ultraviolet rays polymerization initiators or visible light polymerization initiators can be used, when the composition is intended to be used in the mouth, polymerization initiators that will cause polymerization by visible light in the range of wavelength of about 400 to 1200 nm are preferably used with the harmfulness with the light taken into consideration.

The photopolymerization initiator can be an initiator that has a capability of pulling out hydrogen atom even if it is used by itself when the initiator is excited by light, or can be a combination of a photosensitizer that can be excited by light but does not have the capability of pulling out hydrogen atom without a reducing agent. As an example of the former, camphorquinone can be mentioned, but even in this case, it is preferable to use it in combination with a reducing agent to increase the capability of pulling out hydrogen atom. In such a case, the photopolymerization initiator can be regarded as a photosensitizer.

An example of the photosensitizer includes a α-diketone compound such as benzyl and diacetyl. Of these, camphorquinone is preferably used since it exhibits a high polymerization activity.

As a reducing agent that can be used in combination with the photosensitizer in the present invention, a reducing agent that will exhibit the capability of pulling out hydrogen atom when it absorbs energy of excited photosensitizer can be mentioned. As such reducing agent, a tertiary amine is preferably used.

Examples of the tertiary amines include aliphatic amines such as trimethylamine, triethylamine, and tripropylamine; and aromatic amines such as 4-(N,N-dimethylamino)benzoic acid isoamylester, 4-(N,N-dimethylamino)benzoic acid hexylester, 4-(N,N-dimethylamino)benzoic acid heptylester, 4-(N,N-dimethylamino)benzoic acid octylester, 4,4'-bis(dimethylamino)benzophenone, 4,4'-bis(diethylamino)benzophenone, and 4,4'-bis(dibutylamino)-benzophenone. Of these compounds, aromatic tertiary amines are preferably used, and a combination of camphorquinone as photosensitizer with 4,4'-bis(diethylamino)benzophenone as reducing agent is most preferable, because it exhibits excellent visible light polymerizability.

A suitable amount of the photopolymerization initiators to be added in present invention depending on the type of the photopolymerization initiator, or photosensitizer and reducing agent to be used. For example, in the system of combination of camphorquinone and 4,4'-bis(diethylamino)-benzophenone, the amount of the camphorquinone to be added is preferably 0.005 to 30% by weight, and more preferably 0.03 to 20% by weight for the total amount of the radical-polymerizable unsaturated monomers, and the amount of the 4,4'-bis-(diethylamino)benzophenone to be added is preferably in the range of 0.01 to 25% by weight, and more preferably in the range of 0.05 to 20% by weight.

As the redox polymerization initiator, a combination of an amine and a peroxide, a sulfinic acid salt and a peroxide, or an amine, sulfinic acid salt and a peroxide is preferably used.

Examples of the peroxides include diacetyl peroxide, dilauroyl peroxide, distearoyl peroxide, dibenzoyl peroxide, and di-p-chlorobenzoyl peroxide; and dibenzoyl peroxide is particularly preferable since it has excellent polymerizability at ambient temperatures.

Although, as the amine, any of a primary amine, a secondary amine, and a tertiary amine can be used, a tertiary aromatic amine can be used preferably in view of the polymerizability at ambient temperatures.

Examples of preferable aromatic amines include N,N-dimethylaniline, N,N-diethylaniline, N,N-di(β-hydroxyethyl)aniline, N,N-dimethyl-p-toluidine, N,N-diethyl-p-toluidine, N,N-di(β-hydroxyethyl)-p-toluidine, N-methylaniline, N-methyl-p-toluidine, N,N-dimethylanisidine, N,N-diethylanisidine, and diphenylamine; and N,N-dimethyl-p-toluidine and N,N-di(β-hydroxyethyl)-p-toluidine can be mentioned as more preferable amines because they are excellent in polymerizability at ambient temperatures.

Examples of the sulfinic acid salts include sodium p-toluenesulfinate, sodium benzene-sulfinate, potassium benzenesulfinate, calcium benzenesulfinate, barium benzenesulfinate, and ammonium benzenesulfinate. Of these, sodium p-toluenesulfinate is preferably used because it is excellent in polymerizability at ambient temperatures.

When the redox polymerization initiators are used, the amount of initiator to be added is preferably 0.01 to 10% by weight, more preferably 0.05 to 5% by weight of the peroxide for the total amount of the radical-polymerizable unsaturated monomers.

Dental adhesive compositions of the present invention may be blended with inorganic fillers, organic polymers, colorants, polymerization inhibitors, stabilizers to oxidation, and ultra-violet rays absorbers.

Examples of the inorganic fillers include silica powder, quartz powder, and various glass powder. As the organic polymers, polymethyl methacrylate and polystyrene can be exemplified. As the colourants, various kinds of pigments and dyes can be used. The polymerization inhibitors include hydroquinone and methyl phenol.

Dental adhesive compositions of the present invention contain the components (a), (b), (c), and (d), and all of these four components may be stored as blended until they are used. However, if there are some combinations of the components which have lower storage-stability, such components may be stored separately and blended when they are to be used.

For examples, in the case wherein a photopolymerization initiator is used, the component (a) blended with the component (b), and the component (c) blended with the component (d) may be stored separately, and then mixed when they are required to be used.

In the case wherein a redox polymerization initiator is used, the radical-polymerizable unsaturated monomer that is the component (c) is divided into two parts, one of the parts is blended with a peroxide, the other is blended with an aromatic amine or a sulfinate; and component (a) blended with the component (b) may be stored separately and then mixed when they are to be used.

In the present invention, it is possible to use a redox polymerization initiator and a photopolymerization initiator in combination.

The dental adhesive composition of the present invention can be applied to various restorative materials, and can provide excellent bonding properties for composite resins (composite materials prepared by blending polyfunctional monomers with inorganic fillers), thermosetting resins, thermoplastic resins such as polymethyl methacrylate, polysulfone and polycarbonate, and inorganic materials such as various cements, amalgams, alumina, gold, and alloys.

According to the present dental adhesive composition, a troublesome pretreatment using such an etching agent as phosphoric acid that was essential in the prior art when the dentine is required to bond with a restorative material, is not needed, and further a bond strength enough for practical purposes can be obtained.

The present invention will now be described in more detail with reference to Examples, but the present invention is not limited to them.

EXAMPLES

Preparation of Restorative Material A (visible light curing type composite resin)

A mixture (paste) comprising polyfunctional monomers, inorganic fillers, and a visible light polymerization initiator formulated as given below, that is, a visible light curing type composite resin, was prepared in a darkroom, and was named a restorative material A.

| | |
|---|---|
| 2,2-Bis[4-(methacryloyloxyethoxy)phenyl]propane (hereinafter abbreviated to Bis-MEPP) | 8 g |
| Triethylene glycol dimethacrylate (hereinafter abbreviated to 3G) | 12 g |
| Silane-treated quartz powder (having an average diameter of about 4 μm) | 74 g |
| Silicone dioxide finely divided powder (R-972 manufactured by Nippon Aerosil Corp.) | 6 g |
| Camphorquinone | 0.4 g |
| 4-(N,N-dimethylamino)benzoic acid isoamylester | 2 g |

Preparation of Restorative Material B (visible light curing type crown resin)

A mixture comprising polyfunctional monomers, and a visible light polymerization initiator as formulated given below, that is, a visible light curing type crown resin, was prepared in a darkroom, and was named a restorative material B.

| | |
|---|---|
| 2,2-Bis[4-(3-methacryloyloxy-2-hydroxypropoxy)phenyl]propane (hereinafter abbreviated to bis-GMA) | 40 g |
| 3G | 60 g |
| Camphorquinone | 0.7 g |
| 4-(N,N-dimethylamino)benzoic acid isoamylester | 2.8 g |

Procedure for Evaluation of Bonding Properties and Method of Measuring the Bond Strength (1) A flesh cattle fore-tooth immediately after the extraction was cut by a precision cutter (Isomet, manufactured by Bühler Co.) to expose a dentine plane and an enamel plane, the exposed planes were abraded well under running water with No. 1000 water resistant abrasive paper.

(2) A dental adhesive composition was applied to the abraded planes, and if there was a volatile component such as a solvent, the volatile component was evaporated by an air current blown for about 10 sec.

(3) A cylindrical silicon ring having an inner diameter of about 5 mm, a height of about 5 mm, and a wall thickness of about 3 mm was placed on the plane where the dental adhesive component was applied, and then the inside of the silicone ring was filled with a liquid restorative material (Restorative material A) so that the height of the liquid restorative material will become about 3 mm.

(4) The upper end of the silicon ring filled with the restorative material was brought in contact with an irradiation port of a visible light irradiation apparatus (GC Light, manufactured by GC Dental Industries Co.), and visible light was applied thereto for 60 sec to cure the restorative material and the bonding agent.

(5) After about 10 min, the silicon ring was removed to obtain a bonded test piece having the restorative material bonded to the sample plane.

(6) After the bonded test piece was stored in water at 37° C. for a prescribed period, a spacer for bonding test (an acrylic resin rod having the same diameter as that of the restorative material) was bonded to the top of the restorative material by using a quickly polymerizable self-curing resin (Uni Fast, manufactured by GC Dental Industries Co.), then it was set to a prescribed test holder, and a tensile test was carried out to measure the bond strength. The measuring conditions were as follows:

The tensile tester: Tensilon, manufactured by Toyo-Baldwin Co.
The crosshead speed (pulling speed): 0.5 mm/min
Chart speed: 10 mm/min
Full scale: 5 kgw or 20 kgw

Synthesis of Isocyanate-group-containing Urethane Prepolymers

As active hydrogen compound, propylene glycol was used, and by a conventional ring opening copolymerization of propylene oxide and ethylene oxide, various polyether glycols that were different in the molar ratio of the ethylene oxide unit (hereinafter abbreviated to EO) to propylene oxide unit (hereinafter abbreviated to PO) and different in the average molecular weight, and as shown in Table 1 were prepared. Then, these polyether glycols were reacted with tolylene diisocyanate (2,4/2,6 isomer ratio=80/20, hereinafter abbreviated to TDI), 4,4-diphenylmethane diisocyanate (hereinafter abbreviated to MDI), or hexamethylene diisocyanate (hereinafter abbreviated to HDI) used as isocyanating agent at a molar ratio of the polyether glycol to the isocyanating agent being 1:2 to obtain various urethane prepolymers having isocyanate groups at each of the opposite ends, and abbreviation of the prepolymer are shown in Table 1.

TABLE 1

| Abbreviation for urethane prepolymer with isocyanate groups at the opposite ends | Polyether glycol Composition | | | | Isocyanating agent | Property of the prepolymer |
|---|---|---|---|---|---|---|
| | EO/PO | Form of Polymerization | Average molecular weight | Abbreviation | | |
| TPT-1 | 0/100 | — | 500 | PEP-1 | TDI | hydrophobic |
| TPT-2 | " | — | 3,000 | PEP-2 | " | " |
| TPT-3 | " | — | 18,000 | PEP-3 | " | " |
| TPT-4 | 20/80 | random | 800 | PEP-4 | " | " |
| TPT-5 | " | " | 7,000 | PEP-5 | " | " |
| TPT-6 | " | block | 1,500 | PEP-6 | " | " |
| TPT-7 | 40/60 | random | 1,000 | PEP-7 | " | hydrophilic |
| TPT-8 | " | " | 5,000 | PEP-8 | " | " |
| TPT-9 | " | block | 3,000 | PEP-9 | " | " |
| TPT-10 | 60/40 | random | 400 | PEP-10 | " | water soluble |
| TPT-11 | " | " | 2,000 | PEP-11 | " | water |

TABLE 1-continued

| Abbreviation for urethane prepolymer with isocyanate groups at the opposite ends | Polyether glycol Composition | | | | Isocyanating agent | Property of the prepolymer |
|---|---|---|---|---|---|---|
| | EO/PO | Form of Polymerization | Average molecular weight | Abbreviation | | |
| TPT-12 | " | " | 10,000 | PEP-12 | " | soluble water |
| TPT-13 | 80/20 | " | 600 | PEP-13 | " | soluble water |
| TPT-14 | " | " | 1,200 | PEP-14 | " | soluble water |
| MPM-1 | 0/100 | — | 500 | PEP-1 | MDI | soluble hydrophobic |
| MPM-2 | 20/80 | random | 7,000 | PEP-5 | " | " |
| MPM-3 | 40/60 | " | 1,000 | PEP-7 | " | hydrophilic |
| MPM-4 | " | " | 5,000 | PEP-8 | " | " |
| MPM-5 | " | block | 3,000 | PEP-9 | " | " |
| MPM-6 | 60/40 | random | 2,000 | PEP-11 | " | water soluble |
| HPH-1 | 0/100 | — | 500 | PEP-1 | HDI | hydrophobic |
| HPH-2 | 20/80 | random | 7,000 | PEP-5 | " | " |
| HPH-3 | 40/60 | " | 1,000 | PEP-7 | " | hydrophilic |
| HPH-4 | " | " | 5,000 | PEP-8 | " | " |
| HPH-5 | " | block | 3,000 | PEP-9 | " | " |
| HPH-6 | 60/40 | random | 2,000 | PEP-11 | " | water soluble |

Preparation of Mixtures of an Isocyanate-group-containing Urethane Prepolymer and an Isocyanate-group-containing Silane Compound Mixtures of the urethane prepolymer TPT-11 having isocyanate groups at the opposite ends and prepared in the Synthesis of Isocyanate-group-containing Urethane Prepolymers with an isocyanate-group-containing silane compound were prepared by a general-purpose mixer. The compositions and the abbreviations of the mixtures are shown in Table 2.

TABLE 2

| Abbreviation for isocyanate-group-containing urethane prepolymer/ isocyanate-group-containing silane mixture | Abbreviation for isocyanate-group-containing urethane prepolymer | Isocyanate-group-containing compound | Mixing ratio of urethane prepolymer/ silane compound |
|---|---|---|---|
| PS-1 | TPT-11 | $NCO\text{-}(CH_2)_3Si(OC_2H_5)_2$<br>$\vert$<br>$CH_3$ | 20/80 |
| PS-2 | " | " | 60/40 |
| PS-3 | " | " | 95/5 |
| PS-4 | " | " | 99.5/0.5 |
| PS-5 | TPT-11 | $NCO\text{-}(CH_2)_3Si\text{-}(OCH_3)_2$<br>$\vert$<br>$CH_3$ | 20/80 |
| PS-6 | " | " | 60/40 |
| PS-7 | " | " | 95/5 |
| PS-8 | " | " | 99.5/0.5 |
| PS-9 | " | $CH_3Si(NCO)_3$ | 20/80 |
| PS-10 | " | " | 60/40 |
| PS-11 | " | " | 95/5 |
| PS-12 | " | " | 99.5/0.5 |
| PS-13 | " | $CH_2\text{=}CHSi(NCO)_3$ | 20/80 |
| PS-14 | " | " | 60/40 |
| PS-15 | " | " | 95/5 |
| PS-16 | " | " | 99.5/0.5 |

Preparation of Mixtures of Radical-Polymerizable Unsaturated Monomers and a Visible Light Polymerization Initiators Mixtures of various radical-polymerizable unsaturated monomers with a visible photopolymerization initiator were produced in a darkroom by a general-purpose mixer. The compositions and the abbreviations of the mixtures are shown in Table 3.

TABLE 3

| Abbreviation for polymerizable unsaturated monomer/visible light polymerization | Radical-polymerizable unsaturated monomer and the blended amount thereof | | |
|---|---|---|---|
| | Benzyl | 2-Hydroxy ethyl | Triethylene glycol |

TABLE 3-continued

| initiator mixture | methacrylate | methacrylate | dimethacrylate | Bis-GMA | Bis-MEPP |
|---|---|---|---|---|---|
| LC-1 | — | — | 40 | 60 | — |
| LC-2 | — | — | 40 | 60 | — |
| LC-3 | 20 | — | 20 | — | 60 |
| LC-4 | 20 | — | 20 | — | 60 |
| LC-5 | — | 40 | — | — | — |
| LC-6 | — | 40 | — | — | — |
| LC-7 | — | — | — | 60 | 20 |
| LC-8 | — | — | — | 60 | 20 |
| LC-9 | — | 30 | 10 | 30 | — |
| LC-10 | — | 30 | 10 | 30 | — |

| Abbreviation for polymerizable unsaturated monomer/visible light polymerization initiator mixture | Radical-polymerizable unsaturated monomer and the blended amount thereof | | | Visible light polymerization initiator and the blended amount thereof | |
|---|---|---|---|---|---|
| | U-4HA | Methacryloyloxy ethyl phosphate | Dimethacryloyloxyethyl phosphate | Camphorquinone | 4,4-bis (diethylamino) benzophenone |
| LC-1 | — | 2.0 | — | 0.8 | 1.2 |
| LC-2 | — | — | 2.0 | " | " |
| LC-3 | — | 2.0 | — | " | " |
| LC-4 | — | — | 2.0 | " | " |
| LC-5 | 60 | 2.0 | — | " | " |
| LC-6 | 60 | — | 2.0 | " | " |
| LC-7 | 20 | 2.0 | — | 1.2 | 1.6 |
| LC-8 | 20 | — | 2.0 | " | " |
| LC-9 | 30 | 2.0 | — | " | " |
| LC-10 | 30 | — | 2.0 | " | " |

Preparation of Mixtures of Radical-Polymerizable Unsaturated Monomers and a Redox Polymerization Initiator Mixtures of various radical polymerizable unsaturated monomers and a redox polymerization initiator were produced by a general-purpose mixer.

The compositions and the abbreviations of the mixtures are shown below.

| Radical-polymerizable unsaturated monomer/redox polymerization mixture A | |
|---|---|
| U-4HA | 20 g |
| Triethylene glycol dimethacrylate | 10 g |
| Bis-GMA | 50 g |
| 2-Hydroxyethyl methacrylate | 20 g |
| Methacryloyloxyethyl phosphate | 2.0 g |
| Dibenzoyl peroxide | 1.0 g |

| Radical-polymerizable unsaturated monomer/redox polymerization initiator mixture B | |
|---|---|
| 2-Hydroxyethyl methacrylate | 10 g |
| Ethanol | 90 g |
| Dihydroxyethyl-p-toluidine | 0.8 g |
| Sodium p-toluenesulfinate | 0.5 g |

EXAMPLES 1 TO 48

Various isocyanate-group-containing urethane prepolymer/isocyanate-group-containing silane compound mixtures and the radical-polymerizable unsaturated monomer/visible light photopolymerization initiator mixture LC-5, LC-1, or LC-9 were mixed at the same amounts to produce adhesive compositions.

With respect to these adhesive compositions, the bonding properties of the restorative material A to the dentine surface of the cattle tooth that had not been etched were evaluated by using the bonding properties evaluating procedure and the bond strength measuring method mentioned above, and the results are shown in Table 4.

TABLE 4

| | Components and results | | |
|---|---|---|---|
| | Components of adhesive | Average bond strength to dentine (Kg/cm$^2$) | |
| Example No. | Isocyanate-group-containing urethane prepolymer/ isocyanate-group-containing silane compound mixture | Radical-polymerizable unsaturated monomer/ visible light polymerization initiator mixture | After 1 day's storage in water at 37° C. / After 7 day's storage in water at 37° C. |

| Example No. | Isocyanate-group-containing urethane prepolymer/ isocyanate-group-containing silane compound mixture | Radical-polymerizable unsaturated monomer/ visible light polymerization initiator mixture | After 1 day's storage in water at 37° C. | After 7 day's storage in water at 37° C. |
|---|---|---|---|---|
| 1 | PS-1 | LC-5 | 21.3 | 25.1 |
| 2 | PS-2 | " | 24.6 | 26.3 |
| 3 | PS-3 | " | 35.1 | 32.2 |
| 4 | PS-4 | " | 32.0 | 34.5 |
| 5 | PS-5 | " | 25.1 | 26.6 |
| 6 | PS-6 | " | 26.7 | 28.9 |
| 7 | PS-7 | " | 33.9 | 33.6 |
| 8 | PS-8 | " | 37.8 | 40.1 |
| 9 | PS-9 | " | 20.0 | 21.6 |
| 10 | PS-10 | " | 30.5 | 27.4 |

TABLE 4-continued

| Example No. | Isocyanate-group-containing urethane prepolymer/ isocyanate-group-containing silane compound mixture | Radical-polymerizable unsaturated monomer/ visible light polymerization initiator mixture | Average bond strength to dentine (Kg/cm²) | |
|---|---|---|---|---|
| | | | After 1 day's storage in water at 37° C. | After 7 day's storage in water at 37° C. |
| 11 | PS-11 | " | 41.4 | 40.7 |
| 12 | PS-12 | " | 39.2 | 38.3 |
| 13 | PS-13 | " | 22.6 | 27.0 |
| 14 | PS-14 | " | 31.4 | 31.6 |
| 15 | PS-15 | " | 28.7 | 30.3 |
| 16 | PS-16 | " | 35.1 | 32.7 |
| 17 | PS-1 | LC-1 | 23.8 | 24.4 |
| 18 | PS-2 | " | 21.5 | 20.8 |
| 19 | PS-3 | " | 30.7 | 27.9 |
| 20 | PS-4 | " | 36.8 | 35.0 |
| 21 | PS-5 | " | 25.3 | 27.6 |
| 22 | PS-6 | " | 28.1 | 30.4 |
| 23 | PS-7 | " | 30.2 | 28.8 |
| 24 | PS-8 | " | 34.4 | 33.9 |
| 25 | PS-9 | " | 26.0 | 25.8 |
| 26 | PS-10 | " | 34.4 | 34.0 |
| 27 | PS-11 | " | 39.6 | 37.5 |
| 28 | PS-12 | " | 35.9 | 33.8 |
| 29 | PS-13 | " | 20.8 | 25.1 |
| 30 | PS-14 | " | 33.3 | 31.4 |
| 31 | PS-15 | " | 30.5 | 31.3 |
| 32 | PS-16 | " | 34.8 | 33.2 |
| 33 | PS-1 | LC-9 | 22.4 | 25.6 |
| 34 | PS-2 | " | 20.7 | 21.9 |
| 35 | PS-3 | " | 33.4 | 35.2 |
| 36 | PS-4 | " | 38.3 | 36.0 |
| 37 | PS-5 | " | 27.1 | 27.7 |
| 38 | PS-6 | " | 24.0 | 23.7 |
| 39 | PS-7 | " | 31.7 | 33.8 |
| 40 | PS-8 | " | 32.5 | 30.6 |
| 41 | PS-9 | " | 24.2 | 25.3 |
| 42 | PS-10 | " | 38.6 | 36.1 |
| 43 | PS-11 | " | 37.1 | 37.2 |
| 44 | PS-12 | " | 35.7 | 36.0 |
| 45 | PS-13 | " | 23.1 | 25.5 |
| 46 | PS-14 | " | 30.4 | 31.6 |
| 47 | PS-15 | " | 31.7 | 32.0 |
| 48 | PS-16 | " | 33.9 | 30.9 |

*The number of tested samples was 3.

EXAMPLES 49 TO 64

Various isocyanate-group-containing urethane prepolymer/isocyanate-group-containing silane compound mixtures, the radical-polymerizable unsaturated monomer/redox photopolymerization initiator mixture A, and radical-polymerizable unsaturated monomer/redox polymerization initiator mixture B were mixed with the amounts thereof being the same to produce adhesive compositions.

With respect to these adhesive compositions, the bonding properties of the restorative material A were evaluated by the same procedures as in Example 1, and the results are shown in Table 5.

TABLE 4

| Example No. | Isocyanate-group-containing urethane prepolymer/ isocyanate-group-containing silane compound mixture | Radical-polymerizable unsaturated monomer/ visible light polymerization initiator mixture | Average bond strength to dentine (Kg/cm²) | |
|---|---|---|---|---|
| | | | After 1 day's storage in water at 37° C. | After 7 day's storage in water at 37° C. |
| 49 | PS-1 | mixture A and mixture B | 23.7 | 21.6 |
| 50 | PS-2 | " | 25.8 | 27.1 |
| 51 | PS-3 | " | 34.2 | 31.5 |
| 52 | PS-4 | " | 40.6 | 38.5 |
| 53 | PS-5 | " | 21.4 | 24.3 |
| 54 | PS-6 | " | 28.3 | 31.6 |
| 55 | PS-7 | " | 33.6 | 29.1 |
| 56 | PS-8 | " | 30.5 | 34.2 |
| 57 | PS-9 | " | 19.2 | 23.7 |
| 58 | PS-10 | " | 25.1 | 21.8 |
| 59 | PS-11 | " | 29.9 | 34.4 |
| 60 | PS-12 | " | 36.5 | 33.0 |

TABLE 4-continued

| | Components and results | | | |
|---|---|---|---|---|
| | Components of adhesive | | | |
| | Isocyanate-group-containing urethane prepolymer/ | Radical-polymerizable unsaturated monomer/ | Average bond strength to dentine (Kg/cm$^2$) | |
| Example No. | isocyanate-group-containing silane compound mixture | visible light polymerization initiator mixture | After 1 day's storage in water at 37° C. | After 7 day's storage in water at 37° C. |
| 61 | PS-13 | " | 32.4 | 35.3 |
| 62 | PS-14 | " | 26.1 | 29.0 |
| 63 | PS-15 | " | 30.0 | 32.1 |
| 64 | PS-16 | " | 34.4 | 31.8 |

*The number of tested samples was 3.

Preparation of Mixtures of an Isocyanate-group-containing Prepolymer and a Silane Compound Mixtures of the urethane prepolymer TPT-11 having isocyanate groups at the opposite ends prepared in the Synthesis of Isocyanate-group-containing Urethane Prepolymers with a silane compound free from isocyanate groups were prepared by a general-purpose mixer.

The compositions and the abbreviations of the mixtures are shown in Table 6.

Comparative Examples 1 to 6

Example 1 was repeated, except that a mixture of isocyanate-group-containing urethane prepolymer/silane compound free from isocyanate groups was used, to produce adhesive compositions. The bonding properties thereof were evaluated. The results are shown in Table 7.

TABLE 7

| | Components and results | | |
|---|---|---|---|
| | Components of adhesives | | |
| Comparative Example No. | Isocyanate-group-containing urethane prepolymer/silane compound mixture | Radical-polymerizable unsaturated monomer/visible light polymerization initiator mixture | Average bond strength to dentine (Kg/m$^2$)* After 1 day's storage in water at 37° C. |
| 1 | PS-17 | LC-5 | 6.8 |
| 2 | PS-18 | " | 17.3 |
| 3 | PS-19 | " | 14.7 |
| 4 | PS-20 | " | 16.0 |
| 5 | PS-21 | " | 7.9 |
| 6 | PS-22 | " | 13.4 |

*The number of tested samples was 3.

Comparative Examples 7 to 16

Adhesive compositions obtained by blending various radical-polymerizable monomer/visible light photopolymerization initiator mixtures only were evaluated. The results are shown in Table 8.

TABLE 6

| Abbreviation for isocyanate-group containing urethane prepolymer/isocyanate group-containing silane compound mixture | Abbreviation for isocyanate-group-containing urethane prepolymer | Silane compound | Mixing ratio of urethane prepolymer/silane compound |
|---|---|---|---|
| PS-17 | TPT-11 | vinyltriethoxysilane | 60/40 |
| PS-18 | " | vinyltriethoxysilane | 95/5 |
| PS-19 | " | 3-methacryloyloxypropyltrimethoxysilane | 60/40 |
| PS-20 | " | 3-methacryloyloxypropyltrimethoxysilane | 95/5 |
| PS-21 | " | 3-aminopropyltriethoxysilane | 60/40 |
| PS-22 | " | 3-aminopropyltriethoxysilane | 95/5 |

TABLE 8

| Comparative Example No. | Urethane prepolymer with isocyanate groups at the opposite ends/ isocyanate-group-containing silane compound mixture | Radical-polymerizable unsaturated monomer/visible light polymerization initiator mixture | Average bond strength to dentine (Kg/m²)* After 1 day's storage in water at 37° C. |
|---|---|---|---|
| 7 | without | LC-1 | 0.0 |
| 8 | " | LC-2 | 0.0 |
| 9 | " | LC-3 | 0.0 |
| 10 | " | LC-4 | 0.0 |
| 11 | " | LC-5 | 0.0 |
| 12 | " | LC-6 | 0.0 |
| 13 | " | LC-7 | 0.0 |
| 14 | " | LC-8 | 0.0 |
| 15 | " | LC-9 | 0.0 |
| 16 | " | LC-10 | 0.0 |

*The number of tested samples was 3.

EXAMPLES 65 TO 68

By using the adhesive composition obtained in Example 10, the bonding property to various restorative materials was evaluated in the same way as in Example 1. The results are shown in Table 9.

TABLE 9

| Example No. | Restorative material | Average bond strength to dentine *1 (Kg/cm²) |
|---|---|---|
| 65 | restorative material B | 35.4 |
| 66 | commercially available one-paste composite resin *2 | 26.1 |
| 67 | commercially available two-paste composite resin *3 | 27.5 |
| 68 | polymethyl methacrylate *4 | 39.8 |

*1 After 1 day's storage in water at 37° C., the number of tested samples was 3.
*2 Occlusin, manufactured by ICI Co.
*3 Microrest AP, manufactured by GC Dental Industries Co.
*4 Acrypet #VH, manufactured by Mitsubishi Rayon Co. Ltd.

We claim:

1. A dental adhesive composition comprising:
   (a) at least one isocyanate-group-containing urethane prepolymer,
   (b) at least one isocyanate-group-containing silane compound,
   at least one radical-polymerizable unsaturated monomer, and
   (d) at least one initiator selected from the group consisting of redox polymerization initiators and photopolymerization initiators.

2. A dental adhesive composition as claimed in claim 1 wherein the silane compound has the following structural formula:

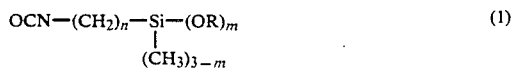

(wherein n is an integer of 1 to 10, m is 2 or 3, and R represents $-CH_3$, $-C_2H_5$, $-OC_2H_4OCH_3$, or $-Cl$).

3. A dental adhesive composition as claimed in claim 1 wherein the silane compound has the following structural formula:

$$R'_p-Si(NCO)_{4-p} \quad (2)$$

(wherein p is an integer of 0 to 3, R' represents methyl group, ethyl group, ethoxy group, phenyl group, vinyl group, α-methyl vinyl group, methacryloyloxyethyl group, acryloyloxyethyl group, methacryloyloxypropyl group, or acryloyloxypropyl group).

4. A dental adhesive composition as claimed in claim 1 wherein the radical-polymerizable unsaturated monomer is a compound selected from the group consisting of benzyl methacrylate, 2-hydroxy ethyl methacrylate, triethylene glycol dimethacrylate, 2,2-bis[4-(3-methacryloyloxy-2-hydroxypropoxy)phenyl]propane,

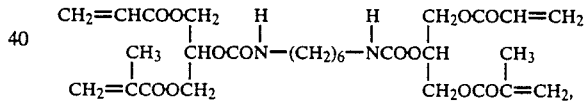

methacryloyloxyethyl phosphate, and dimethacryloyloxyethyl phosphate.

5. A dental adhesive composition as claimed in claim 1 wherein 0.1 to 30% by weight based on the weight of total amount of the radical-polymerizable unsaturated monomers of the polymerizable phosphate is added.

6. A dental adhesive composition as claimed in claim 1 wherein camphorquinone is used as a photosensitizer of the photopolymerization initiator.

7. A dental adhesive composition as claimed in claim 1 wherein 4,4'-bis(diethylamino)benzophenone is used as a reducing agent of the photopolymerization initiator.

8. A dental adhesive composition as claimed in claim 1 wherein N,N-dimethyl-p-toluidine or N,N-di(β-hydroxyethyl)-p-toluidine is used in combination with a peroxide as the redox polymerization initiator.

9. A dental adhesive composition as claimed in claim 1 wherein sodium p-toluene sulfinate is used in combination with a peroxide as the redox polymerization initiator.

10. A dental adhesive composition as claimed in claim 1 wherein dibenzyl peroxide is used as a component of the redox polymerization initiator.

* * * * *